United States Patent [19]

Plank et al.

[11] 4,016,245

[45] Apr. 5, 1977

[54] CRYSTALLINE ZEOLITE AND METHOD OF PREPARING SAME

[75] Inventors: Charles J. Plank, Woodbury; Edward J. Rosinski, Pedricktown, both of N.J.; Mae K. Rubin, Bala Cynwyd, Pa.

[73] Assignee: Mobil Oil Corporation, New York, N.Y.

[22] Filed: Nov. 29, 1974

[21] Appl. No.: 528,061

Related U.S. Application Data

[63] Continuation-in-part of Ser. No. 393,767, Sept. 4, 1973, abandoned, which is a continuation-in-part of Ser. No. 358,192, May 7, 1973, abandoned.

[52] U.S. Cl. .............................. 423/328; 423/329; 260/448 C; 260/326.61; 260/583 P
[51] Int. Cl.$^2$ ............... C01B 33/28; C07F 7/02
[58] Field of Search .......... 423/328, 329, 330, 118; 260/448 C, 326.61, 583 P, 583 R; 252/455 Z

[56] References Cited

UNITED STATES PATENTS

| | | | |
|---|---|---|---|
| 3,578,398 | 5/1971 | Jenkins | 423/328 |
| 3,642,434 | 2/1972 | Dwyer | 423/329 |
| 3,692,470 | 9/1972 | Ciric | 423/328 |
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |

OTHER PUBLICATIONS

Barrer et al., "Chemical Society Journal," 1964, Part 1, pp. 485–497.
Barrer et al., "The American Mineralogist," vol. 50, 1965, pp. 484–489.
Wise, "The American Mineralogist," vol. 54, 1969, pp. 887–895.

*Primary Examiner*—Edward J. Meros
*Attorney, Agent, or Firm*—Charles A. Huggett; Raymond W. Barclay; Dennis P. Santini

[57] ABSTRACT

A new crystalline zeolite, designated ZSM-35, a method of making same and the use thereof in catalytic conversion of hydrocarbons is the subject of this application. The new zeolite has a composition, in the anhydrous state, expressed in terms of mole ratios of oxides as follows:

$$(0.3-2.5)R_2O:(0-0.8)M_2O:Al_2O_3:>8\ SiO_2$$

wherein R is an organic nitrogen-containing cation and M is an alkali metal cation, and is characterized by a specified X-ray powder diffraction pattern.

13 Claims, 6 Drawing Figures

CRYSTALLINE ZEOLITE AND METHOD OF PREPARING SAME

CROSS-REFERENCE TO RELATED APPLICATIONS

This is a continuaton-in-part of application Ser. No. 393,767, filed Sept. 4, 1973, which is a continuation-in-part of application Ser. No. 358,192, filed May 7, 1973, both now abandoned.

BACKGROUND OF THE INVENTION

1. Field of the Invention

This invention relates to a novel crystalline aluminosilicate, to a method for its preparation and to its use in catalytic conversion of hydrocarbons.

2. Description of the Prior Art

Zeolitic materials, both natural and synthetic, have been demonstrated in the past to have catalytic properties for various types of hydrocarbon conversions. Certain zeolitic materials are ordered, porous crystalline aluminosilicates having a definite crystalline structure within which there are a large number of smaller cavities which may be interconnected by a number of still smaller channels. These cavities and channels are precisely uniform in size. Since the dimensions of these pores are such as to accept for absorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the starting of oxygen atoms whereby the ratio of the total aluminum and silicon atoms to oxygen is 1:2. The electrovalence of the tetrahedra containing aluminum is balanced by the inclusion in the crystal of a cation, for example, an alkali metal or an alkaline earth metal cation. This can be expressed wherein the ratio of aluminum to the number of various cations, such as Ca/2, Sr/2, Na, K or Li is equal to unity. One type of cation may be exchanged either entirely or partially by another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic aluminosilicates. These aluminosilicates have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752) and zeolite ZSM-5 (U.S. Pat. No. 3,702,886), merely to name a few.

One such crystalline aluminosilicate, a rare natural zeolite, is ferrierite. Ferrierite has been described by Graham (Roy. Soc. Canada, Proc. and Trans., 3rd Ser., 12, 185–190) and by Staples (Am. Mineral. 40, 1095-99). The formula of the natural mineral ferrierite is given as $(Na, K)_4 Mg_2 (Si_{30}Al_6) O_{72}(OH)_2 \cdot 0.18 H_2O$. Barrer and Marshall (Am. Mineral 50,484-85) in 1965 reexamined the X-ray powder diffraction pattern of a strontium zeolite Sr-D, synthesized by Barrer and Marshall in 1964 (J. Chem. Soc., 485–89) and concluded that it was closely related to natural ferrierite. A synthetic sodium form was briefly described by Senderov (Geokhimiya 9, 820–29) and a Ca-Na form of ferrierite produced by Coombs, Ellis, Fyfe and Taylor (Geochem. Cosmochim. Acta 17, 53–107) was not identified as such.

SUMMARY OF THE INVENTION

The present invention relates to a novel synthetic crystalline aluminosilicate, hereinafter designated "zeolite ZSM-35" or simply "ZSM-35", to methods for its preparation and to hydrocarbon conversion conducted therewith. The ZSM-35 composition has a characteristic X-ray diffraction pattern, the values of which are set forth in Table 1, hereinafter. The ZSM-35 composition can also be identified, in terms of mole ratios of oxides and in the anhydrous state, as follows:

$$(0.3–2.5)R_2O:(0–0.8)M_2O : Al_2O_3 : > 8 SiO_2$$

wherein R is an organic nitrogen-containing cation derived from ethylenediamine or pyrrolidine and M is an alkali metal cation, and is characterized by a specified X-ray powder diffraction pattern. It will be noticed that the ratio of $R_2O$ to $Al_2O_3$ may exceed unity in this material due to the occlusion of excess organic species ($R_2O$) within the zeolite pores.

ZSM-35 can further be characterized by its sorptive capacity at 90° C, as will be hereinafter established.

In a preferred synthesized form, the zeolite has a formula, in terms of mole ratios of oxides and in the anhydrous state, as follows:

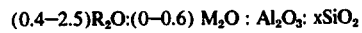

$$(0.4–2.5)R_2O:(0–0.6) M_2O : Al_2O_3: xSiO_2$$

wherein R' is an organic nitrogen-containing cation derived from ethylenediamine or pyrrolidine, M is an alkali metal, especially sodium, and x is from greater than 8 to about 50.

The original cations of the as synthesized ZSM-35 can be replaced in accordance with techniques well known in the art, at least in part, by ion exchange with other cations. Preferred replacing cations include metal ions, ammonium ions, hydrogen ions and mixtures thereof. Particularly preferred cations are those which render the zeolite catalytically active especially for hydrocarbon conversion. These include hydrogen, rare earth metals, aluminum, metals of Groups IIA, IIIB, IVB, VIB, VIII, IB, IIB, IIIA, IVA.

The synthetic ZSM-35 zeolite possesses a definite distinguishing crystalline structure whose x-ray diffraction pattern shows substantially the significant lines set forth in Table 1. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE 1

| d(A) | I/Io |
|---|---|
| 9.6 ± 0.20 | Very Strong-Very Very Strong |
| 7.10 ± 0.15 | Medium |
| 6.98 ± 0.14 | Medium |
| 6.64 ± 0.14 | Medium |

TABLE 1-continued

| d(A) | I/Io |
|---|---|
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium-Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak-Medium |
| 3.14 ± 0.06 | Weak-Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 I/Io, where Io is the intensity of the strongest line or peak, and d (obs.), the interplanar spacing in Angstrom units, corresponding to the recorded lines, were calculated. It should be understood that this X-ray diffraction pattern is characteristic of all the species of ZSM-35 compositions. Ion exchange of the sodium ion with cations reveals substantially the same pattern with some minor shifts in interplanar spacing and variation in relative intensity. Other minor variations can occur depending on the silicon to aluminum ration of the particular sample, as well as if it has previously been subjected to thermal treatment.

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C) is less than 10, whereas that ratio for the natural ferrierite is substantially greater than 10, for example, as high as 34 or higher.

While synthetic ZSM-35 zeolites may be used in a wide variety of hydrocarbon conversion reactions, they are notably useful in the processes of polymerization, aromatization and cracking. Other hydrocarbon conversion processes for which ZSM-35 may be utilized in one or more of its active forms include, for example, hydrocracking and converting light aliphatics to aromatics such as in U.S. Pat. No. 3,760,024.

Synthetic ZSM-35 zeolites can be used either in the organic nitrogen-containing and alkali metal containing form, the alkali metal form and hydrogen form or another univalent or multivalent cationic form. They can also be used in intimate combination with a hydrogenating component such as tungsten, vanadium, molybdenum, rhenium, nickel, cobalt. chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to ZSM-35 such as, for example, by, in the case of platinum, treating the zeolite with a platinum metal-containing ion. Thus, suitable platinum compounds for this purpose include chloroplatinic acid, platinous chloride and various compounds containing the platinum amine complex. Combinations of metals and methods for their introduction can also be used.

As prepared, R can be one or more of a variety of organic nitrogen-containing cations present in quantity of not less than 40% of whole, examples of which include those cations derived from pyrrolidine and ethylenediamine.

Also, M can be one or more of a variety of alkali metal cations, suitably defined as including all alkali metal ions derived from alkali metal oxide or hydroxide as well as alkali metal ions included in alkali metal silicates and aluminates (not including alkali metal salts such as sodium chloride or sodium sulfate which may be derived from neutralization of added inorganic acids such as HCl or $H_2SO_4$ or acid salts such as $Al_2(SO_4)_3$). Non-limiting examples of such suitable alkali metal ions include sodium and potassium.

Synthetic ZSM-35, when employed either as an adsorbent or as a catalyst in a hydrocarbon conversion process, should be dehydrated at least partially. This can be done by heating to a temperature in the range of 200° to 600° C in an inert atmosphere, such as air, nitrogen, etc. and at atmospheric or subatmospheric pressures for between 1 and 48 hours. Dehydration can also be performed at lower temperature merely by placing the catalyst in a vacuum, but a longer time is required to obtain a sufficient amount of dehydration.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH−/SiO2 | 0.05–0.5 | 0.07–0.49 |
| H2O/OH− | 41–500 | 100–250 |
| SiO2/Al2O3 | 8.8–200 | 12–60 | wherein R is an organic nitrogen-containing cation derived from ethylenediamine or pyrrolidine and M is an alkali metal ion, and maintaining the mixture until crystals of the zeolite are formed. (The quantity of OH− is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° F for a period of time of from about 6 hours to about 100 days. A more preferred temperature range is from about 150° to about 400° F with the amount of time at a temperature in such range being from about 6 hours to about 80 days.

The digestion of the gel particles is carried out until crystals form. The solid product is separated from the reaction medium, as by cooling the whole to room temperature, filtering and water washing.

The crystalline product is dried, e.g. at 230° F, for from about 8 to 24 hours. Of course, milder conditions may be employed if desired, e.g. room temperature under vacuum.

The composition for the synthesis of synthetic ZSM-35 can be prepared utilizing materials which can supply the appropriate oxide. Such compositions include aluminates, alumina, silicates, silica hydrosol, silica gel, silicic acid and hydroxides. It will be understood that each oxide component utilized in the reaction mixture for preparing ZSM-35 can be supplied by one or more essential reactants and they can be mixed together in any order. For example, any oxide can be supplied by an aqueous solution, sodium hydroxide or by an aqueous solution of a suitable silicate; the organic nitrogen-containing cation can be supplied by a compound of that cation, such as, for example, the hydroxide or a salt, as well as by the indicated amines. The reaction mixture can be prepared either batchwise or continuously. Crystal size and crystallization time of the ZSM-35 composition will vary with the nature of the reaction mixture employed.

Figure 1:
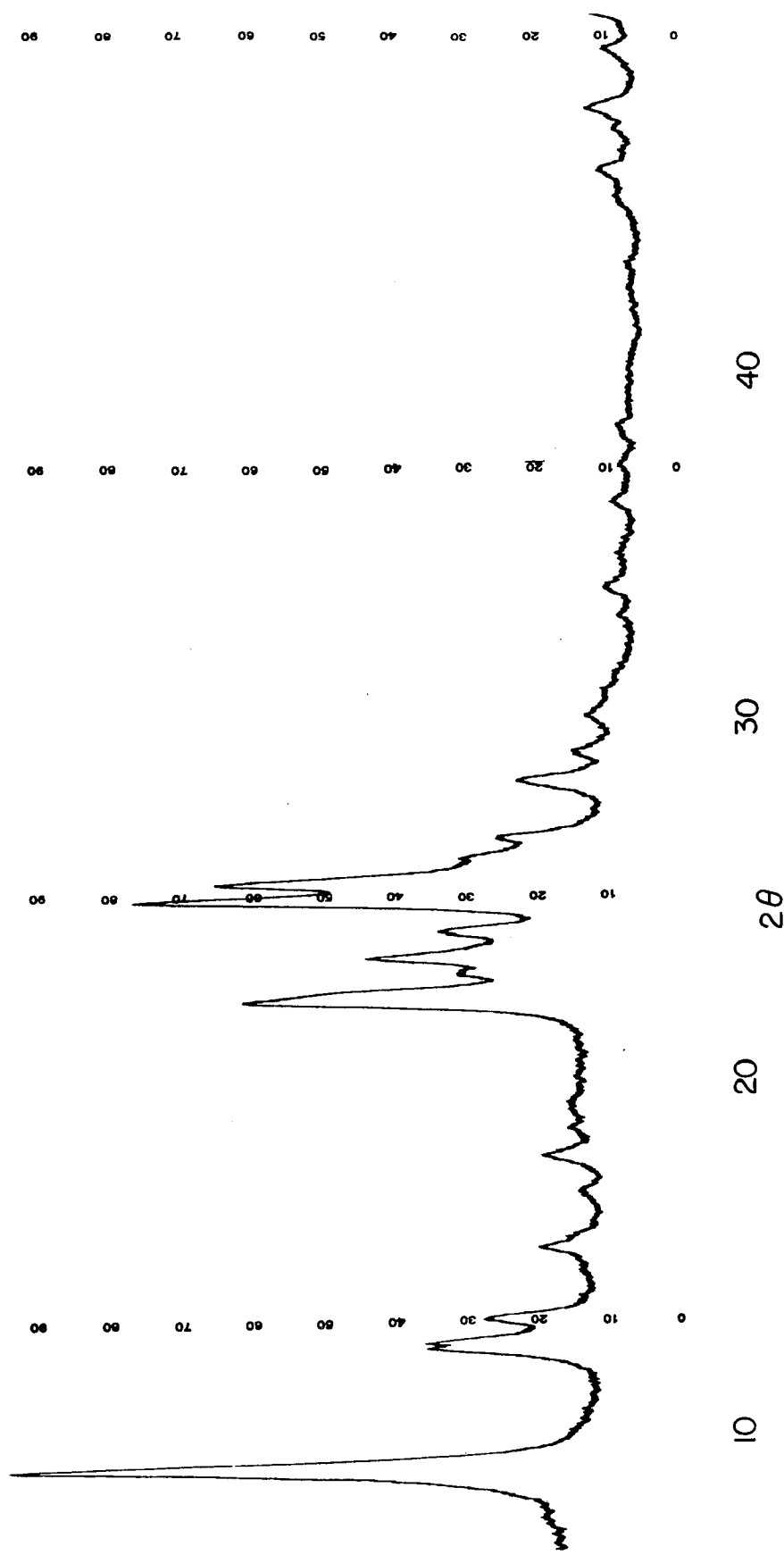
FIG. 1 is a photographically reduced copy of the X-ray powder diffraction pattern for the crystalline aluminosilicate zeolite ZSM-35 prepared in Example 1, hereinafter presented.

In the figures, the numbers on the bottom scale thereof indicate degrees 2 theta. Also, the tracings of FIGS. 3, 5 and 6 were obtained at a relatively high recorder sensitivity setting in order that the weaker peaks would show up more visibly. This high sensitivity setting has caused some of the stronger peaks to go off scale somewhat. However, the values listed in Tables 3 and 6 make the definition of the off-scale stronger peaks clear.

DESCRIPTION OF SPECIFIC EMBODIMENTS

Synthetic ZSM-35 can have the orignial cations associated therewith replaced by a wide variety of other cations according to the techniques well known in the art. Typical replacing cations include hydrogen, ammonium and metal cations including mixtures thereof. Of the replacing metallic cations, particular preference is given to cations of metals such as rare earth, Mn, Ca, Mg, Zn, Cd, Pd, Ni, Co, Ti, Al, Sn, Fe and Co.

Typical ion exchanger techniques would be to contact the synthetic ZSM-35 zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the air salt solution of the desired replacing cation, the zeolite is then preferably washed with water and dried at a temperature ranging from 150° to about 600° F and thereafter may be calcined in air or other inert gas at temperatures ranging from about 500° F to 1500° F for periods of time ranging from 1 to 48 hours or more to produce a catalytically-active thermal decomposition product thereof.

Regardless of the cations replacing the alkali metal in the synthesized of the ZSM-35, the spacial arrangement of the aluminum, silicon and oxygen atoms which form the basic crystal lattices of ZSM-35 remains essentially unchanged by the described replacement of alkali metal as determined by taking an X-ray powder diffraction pattern of the ion-exchanged material.

The aluminosilicate prepared by the instant invention is formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the aluminosilicate can be extruded before drying or dried or partially dried and then extruded.

In the case of many catalysts, it is desired to incorporate the ZSM-35 with another material resistant to the temperatures and other conditions employed in organic conversion processes. Such matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides. Use of a material in conjunction with the ZSM-35, i.e. combined therewith, which is active, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. Frequently, zeolite materials have been incorporated into naturally occurring clays, e.g. bentonite and kaolin. These materials, i.e. clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the synthetic ZSM-35 catalyst include the montmorillonite and kaolin family, which families include the sub-bentonites, and the kaolins commonly known as Dixie, McNanee, Georgia and Florida clays or others in which the main mineral constituents is halloysite, kaolinite, dickite, nacrite, or anauxite. Such clays can be used in the raw state as originally mined or initially subjected to calcination, acid treatment or chemical modification.

In addition to the foregoing materials, the ZSM-35 catalyst can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used. The relative proportions of finely divided crystalline aluminosilicate ZSM-35 and inorganic oxide gel matrix vary widely with the crystalline aluminosilicate content ranging from about 1 to about 90 percent by weight and more usually in the range of about 2 to about 50 percent by weight of the composite.

In employing the ZSM-35 catalyst of this invention for polymerization of olefin containing liquid or gaseous charge stocks, such charge stocks can be polymerized at temperatures between 550 and 850° F at an hourly space velocity of between 0.5 and 50 WHSV and a pressure between 0.1 and 800 psig.

In employing the catalyst of the present invention for aromatization of gaseous or liquid charge stocks which may be olefinic or paraffinic with or without aromatics present, such stocks can be aromatized at temperatures between 800 and 1200° F and pressures from 1 to 10 atmospheres and space velocities between 0.1 and 10 WHSV.

In order to more fully illustrate the nature of the invention and the manner of practicing same, the following examples are presented.

In the examples which follow, whenever adsorption data are set forth for comparison of sorptive capacities for water, cyclohexane and n-hexane, they were determined as follows:

A weighed sample of the calcined zeolite was contacted with the desired pure adsorbate vapor in an adsorption chamber, evacuated to 12 mm when checking capacity for water and 20 mm when checking capacity for cyclohexane and n-hexane, pressures less than the vapor-liquid equilibrium pressure of the respective absorbate at room temperature. The pressure was kept constant (within about ±0.5 mm) by addition of adsorbate vapor controlled by a manostat during the adsorption period which did not exceed about eight hours. As adsorbate was adsorbed by the zeolite, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample.

When the sorptive capacities for 2-methylpentane and n-hexane were measured for distinguishing comparisons of ratios of n-hexane/2-methylpentane sorption, a weighed sample of zeolite was heated to 600° C and held at that temperature until the evolution of basic nitrogenous gases ceased. The zeolite was then cooled and the sorption test run essentially as above with the sorption being conducted at 90° C and the sorbate being chilled at 0° C.

EXAMPLE 1

Illustrating preparation of synthetic zeolite ZSM-35, a first solution comprising 3.3 g sodium aluminate (41.8% $Al_2O_3$, 31.6% $Na_2O$ and 24.9% $H_2O$), 87.0 g $H_2O$ and 0.34 g NaOH (50% solution with water) was prepared. The organic material pyrrolidine was added to the first solution in 18.2 g quantity to form a second solution. Thereupon, 82.4 g colloidal silica (29.5% $SiO_2$ and 70.5% $H_2O$) was added to the second solution and mixed until a homogeneous gel was formed. This gel was composed of the following components in mole ratios:

$\dfrac{R^+}{R^+ + M^+}$   0.87, wherein M is sodium and $R^+$ is the pyrrolidine ion.

$\dfrac{OH^-}{SiO_2}$   0.094 (Not including any contribution of $OH^-$ from pyrollidine)

$\dfrac{H_2O}{OH^-}$   210 (Not including any contribution of $OH^-$ from pyrollidine)

$\dfrac{SiO_2}{Al_2O_3}$   30.0

The mixture was maintained at 276° F for 17 days, during which time crystallization was complete. The product crystals were filtered out of solution and water washed for approximately 16 hours on continuous wash line.

X-ray analysis of the crystalline product proved the crystals to have a diffraction pattern as shown below:

| 2 Times Theta | d(A) | I/Io |
|---|---|---|
| 7.70 | 11.48 | 5 |
| 9.28 | 9.53 | 127 |
| 12.52 | 7.07 | 25 |
| 12.78 | 6.93 | 25 |
| 13.40 | 6.61 | 27 |
| 15.38 | 5.76 | 12 |
| 15.62 | 5.67 | 4 |
| 16.90 | 5.25 | 4 |
| 17.92 | 4.95 | 10 |
| 18.75 | 4.73 | 5 |
| 19.40 | 4.58 | 4 |
| 22.32 | 3.98 | 63 |
| 22.60 | 3.93 | 39 |
| 23.13 | 3.85 | 20 |
| 23.60 | 3.77 | 51 |
| 23.85 | 3.73 | 12 |
| 24.30 | 3.66 | 33 |
| 25.21 | 3.53 | 100 |
| 25.70 | 3.47 | 80 |
| 26.30 | 3.39 | 28 |
| 26.92 | 3.31 | 24 |
| 28.53 | 3.13 | 18 |
| 29.34 | 3.04 | 8 |
| 30.25 | 2.954 | 6 |
| 30.65 | 2.917 | 2 |
| 31.00 | 2.885 | 4 |
| 31.41 | 2.848 | 3 |
| 33.15 | 2.702 | 3 |
| 33.98 | 2.638 | 7 |
| 34.40 | 2.607 | 3 |
| 34.87 | 2.573 | 4 |
| 35.35 | 2.539 | 2 |
| 36.33 | 2.473 | 4 |
| 36.77 | 2.444 | 2 |
| 37.45 | 2.401 | 4 |
| 38.33 | 2.348 | 5 |
| 39.00 | 2.309 | 2 |
| 39.47 | 2.283 | 2 |
| 42.30 | 2.137 | 2 |
| 42.90 | 2.108 | 2 |
| 44.75 | 2.025 | 5 |
| 45.56 | 1.991 | 8 |
| 46.20 | 1.965 | 3 |
| 46.70 | 1.945 | 4 |
| 47.30 | 1.922 | 9 |

| 2 Times Theta | d(A) | I/Io |
|---|---|---|
| 48.90 | 1.862 | 6 |

A photographically reduced exact copy of the X-ray powder diffraction pattern tracing for the zeolite ZSM-35 prepared in Example 1 is shown in FIG. 1 of the drawings.

Chemical anaylsis of the crystalline product led to the following compositional figures:

| Composition | Wt. % | Mole Ratio on $Al_2O_3$ Basis | |
|---|---|---|---|
| N | 1.87 | — | |
| Na | 0.25 | — | |
| $Al_2O_3$ | 5.15 | 1.0 | |
| $SiO_2$ | 90.7 | 29.9 | |
| $N_2O$ | — | 1.54 | |
| $Na_2O$ | — | 0.11 | |
| $H_2O$ | — | 9.90 | (from $H_2O$ adsorption |

Physical analysis of the crystalline product of Example 1 calcined 16 hours at 1000° F showed it to have a surface area of 304 m²/g and adsorption tests (conducted as hereinbefore described) produced the following results:

| Adsorption | Wt. % |
|---|---|
| Cyclohexane | 1.0 |
| n-Hexane | 5.4 |
| Water | 9.0 |
| n-Hexane/2-methylpentane (90° C) | = 2.64 |

EXAMPLE 2

A batch of ZSM-35 was prepared by first making a solution of 101.6g sodium silicate (28.8% $SiO_2$, 8.9% $Na_2O$ and 62.2% $H_2O$), 6.5g NaOH (50% solution) and 59.8g $H_2O$. Then 30.0g ethylenediamine was added to the first solution. To this mixture was added a solution comprised of 19.4g $Al_2(SO_4)_3 \cdot 18H_2O$, 4.5g $H_2SO_4$ and 174g $H_2O$, and the resultant gel was mixed until homogeneous. This gel was composed of the following components in mole ratios:

$\dfrac{R^+}{R^+ + M^+}$ 0.82, wherein M is sodium and R is $H_2N(CH_2)_2NH_2$ $\dfrac{OH^-}{SiO_2}$ 0.22

$\dfrac{H_2O}{OH^-}$ 152

$\dfrac{SiO_2}{Al_2O_3}$ 16.7

The gel mixture was maintained at 210° F for 62 days, during which time crystallization was complete. The product crystals were filtered out of solution and water washed.

X-ray analysis of the crystalline product proved the crystals to have a diffraction pattern as shown in Table 1 and chemical analysis proved them to have a mole ratio of $SiO_2$ to $Al_2O_3$ of 14.4.

In the aforementioned sorption test for measuring the distinctive sorption capacity ratio of n-hexane/2-methylpentane at 90° C, the sample of ZSM-35 prepared according to this example sorbed 5.1 weight percent n-hexane and 2.8 weight percent 2-methylpentane (n-hexane/2-methylpentane = 1.82).

EXAMPLE 3

A quantity of natural ferrierite, with a mole ratio of $SiO_2$ to $Al_2O_3$ of 12 was calcined at 1000° F for 10 hours and exchanged with ammonium chloride solution. The exchange ferrierite was then dried at 230° F for 16 hours and calcined at 1000° F for 10 hours to produce the hydrogen form of the zeolite (H-ferrierite). Also, the zeolite ZSM-35 of Example 2 was processed as above to produce an HZSM-35 zeolite.

EXAMPLE 4

The H-ferrierite and HZSM-35 products of Example 3 were subjected to a modified version of the alpha-test described by P. B. Weisz and J. N. Miale in *Journal of Catalysis*, 4, 527–529 (1965) to determine cracking rate of n-hexane with the liquid hourly space velocity maintained at 1.0 and the temperature maintained at 800° F. The alpha-test of this example differs from that described by Weisz and Miale only in that the feed here is a mixture of n-hexane, 3-methylpentane and 2,2-dimethylbutane. The results, indicating vast superiority of HZSM-35 in comparison with H-ferrierite in cracking activity, were as follows:

| Catalyst | n-Hexane Cracking Rate α (5 minutes after commencement of flow) |
|---|---|
| H-ferrierite | 170 |
| HZSM-35 | 420 |

EXAMPLE 5

A batch of the H-ferrierite product of Example 3 was subjected to the aforementioned sorption test for measuring the distinctive sorption capacity ratio of n-hexane/2-methylepentane at 90° C. Results of that test showed sorption of 3.4 weight percent n-hexane and less than 0.1 weight percent 2-methylpentane (n-hexane/2-methylpentane = >34.)

EXAMPLE 6–8

The synthetic crystalline zeolite ZSM-35 preparations of Examples 6–8 are presented hereby in tabular form in Tables 2 and 2A. These examples were prepared while using ethylenediamine as the organic nitrogen-containing cation source, wherein R is $H_2N(C_2H_2)_2NH_2$ and M is sodium. X-ray analysis of the products of each of Examples 6–8 proved them to have the diffraction patterns shown in Table 3.

TABLE 2

ZSM-35 SYNTHESIS FROM ETHYLENEDIAMINE

| Example | Preparation Notes | Starting Gel, Molar Ratio | | | | Crystallization | |
|---|---|---|---|---|---|---|---|
| | | $R^+/R^+ + M^+$ | $OH^-/SiO_2$ | $SiO_2/Al_2O_3$ | $H_2O/OH^-$ | Temp.° F | Time, Days |
| 6 | Components of Example 1(2) | 0.87 | 0.19 | 14.6 | 205 | 350 | 10 |
| 7 | Components of Example 1(2) | 0.89 | 0.15 | 16.2 | 244 | 350 | 5 |
| 8 | (1) | 0.64 | 0.404 | 50.0 | 81.6 | 210 | 41 |

(1) Components:
First Solution
  Sodium silicate (28.8% $SiO_2$, 8.9% $Na_2O$ and 62.2% $H_2O$)
  Sodium hydroxide
  Water
Second Solution
  $Al_2(SO_4)_3 \cdot 18H_2O$
  $H_2SO_4$
  Water
Third Solution
  Contents of First Solution
  Ethylenediamine
Starting Gel
  Contents of Third Solution
  Contents of Second Solution (2) components of zeolite preparation reaction mixture excluding the source of organic nitrogen-containing cation.

TABLE 2A

ZSM-35 SYNTHESIS FROM ETHYLENEDIAMINE

| | Final Product Analysis per mole $Al_2O_3$ | | | | Final Product Sorption wt. % | | Surface Area |
|---|---|---|---|---|---|---|---|
| Example | $N_2O$ | $Na_2O$ | $SiO_2$ | $H_2O$ | $Cy-C_6$ | $n-C_6$ | $m^2gm$ |
| 6 | 2.18 | 0.01 | 19.8 | 11.6 | 1.0 | 5.0 | 283 |
| 7 | 1.87 | — | 15.2 | 11.6 | 1.1 | 5.7 | 299 |
| 8 | 1.94 | — | 21.4 | 11.6 | 1.4 | 6.5 | 334 |

TABLE 3

X-Ray Diffraction Patterns of ZSM-35 Prepared in Example 6

| 2 Times Theta | d(A) | I/Io |
|---|---|---|
| 7.80 | 11.33 | 1 |
| 9.22 | 9.59 | 124 |
| 12.50 | 7.08 | 26 |
| 12.68 | 6.98 | 38 |
| 13.35 | 6.63 | 22 |
| 13.75 | 6.44 | 1 |
| 15.34 | 5.78 | 10 |
| 15.60 | 5.68 | 6 |
| 17.85 | 4.97 | 6 |
| 18.35 | 4.83 | 1 |
| 18.72 | 4.74 | 3 |
| 19.42 | 4.57 | 1 |
| 22.29 | 3.99 | 77 |
| 22.60 | 3.93 | 50 |
| 23.12 | 3.85 | 28 |
| 23.55 | 3.78 | 55 |
| 23.80 | 3.74 | 6 |
| 24.32 | 3.66 | 33 |
| 25.14 | 3.54 | 100 |
| 25.61 | 3.48 | 83 |
| 26.39 | 3.38 | 15 |
| 26.92 | 3.31 | 17 |
| 28.45 | 3.14 | 15 |
| 29.30 | 3.05 | 17 |
| 30.30 | 2.950 | 8 |
| 30.90 | 2.894 | 7 |
| 31.50 | 2.840 | 3 |
| 33.09 | 2.707 | 4 |
| 33.88 | 2.646 | 7 |
| 34.37 | 2.609 | 2 |
| 34.79 | 2.579 | 3 |
| 35.30 | 2.542 | 2 |
| 36.29 | 2.475 | 6 |
| 36.70 | 2.449 | 1 |
| 37.35 | 2.408 | 4 |
| 37.65 | 2.389 | 1 |
| 38.35 | 2.347 | 4 |
| 39.05 | 2.306 | 3 |
| 39.45 | 2.284 | 2 |
| 39.92 | 2.258 | 2 |

TABLE 3-continued

X-Ray Diffraction Patterns of ZSM-35 Prepared in Example 6

| 2 Times Theta | d(A) | I/Io |
|---|---|---|
| 40.29 | 2.238 | 3 |
| 41.51 | 2.175 | 1 |
| 42.14 | 2.144 | 3 |
| 42.85 | 2.110 | 3 |
| 44.78 | 2.024 | 5 |
| 45.50 | 1.994 | 11 |
| 46.25 | 1.963 | 1 |
| 46.65 | 1.947 | 4 |
| 47.29 | 1.922 | 12 |
| 48.77 | 1.867 | 8 |
| 49.78 | 1.832 | 3 |
| 50.60 | 1.804 | 3 |
| 51.35 | 1.779 | 4 |
| 51.65 | 1.770 | 7 |
| 52.71 | 1.737 | 2 |
| 53.74 | 1.706 | 3 |
| 54.90 | 1.672 | 1 |
| 55.35 | 1.660 | 3 |
| 55.67 | 1.651 | 1 |
| 56.09 | 1.640 | 1 |
| 56.70 | 1.623 | 1 |
| 57.00 | 1.616 | 1 |
| 57.35 | 1.607 | 3 |
| 58.60 | 1.575 | 2 |
| 59.84 | 1.546 | 2 |

TABLE 3

X-Ray Diffraction Patterns of ZSM-35 Prepared in Example 7

| 2 Times Theta | d(A) | I/Io |
|---|---|---|
| 9.22 | 9.59 | 106 |
| 12.40 | 7.14 | 29 |
| 12.60 | 7.03 | 25 |
| 13.26 | 6.68 | 17 |
| 15.30 | 5.79 | 9 |

TABLE 3-continued

X-Ray Diffraction Patterns of ZSM-35 Prepared in Example 7

| 2 Times Theta | d(A) | I/Io |
|---|---|---|
| 15.55 | 5.70 | 6 |
| 17.80 | 4.98 | 4 |
| 18.28 | 4.85 | 1 |
| 18.69 | 4.75 | 3 |
| 19.32 | 4.59 | 1 |
| 22.21 | 4.00 | 48 |
| 22.51 | 3.95 | 46 |
| 23.05 | 3.86 | 19 |
| 23.46 | 3.79 | 50 |
| 23.74 | 3.75 | 8 |
| 24.25 | 3.67 | 34 |
| 25.05 | 3.55 | 100 |
| 25.53 | 3.49 | 77 |
| 26.30 | 3.39 | 18 |
| 26.84 | 3.32 | 17 |
| 28.35 | 3.15 | 29 |
| 29.21 | 3.06 | 12 |
| 30.20 | 2.959 | 9 |
| 30.80 | 2.903 | 6 |
| 31.40 | 2.849 | 2 |
| 32.98 | 2.716 | 5 |
| 33.78 | 2.653 | 5 |
| 34.22 | 2.620 | 2 |
| 34.72 | 2.584 | 4 |
| 35.27 | 2.545 | 2 |
| 36.17 | 2.483 | 6 |
| 36.72 | 2.447 | 1 |
| 37.20 | 2.417 | 6 |
| 37.70 | 2.386 | 1 |
| 38.25 | 2.353 | 4 |
| 38.98 | 2.310 | 2 |
| 39.32 | 2.291 | 2 |
| 39.80 | 2.265 | 1 |
| 39.98 | 2.255 | 1 |
| 40.16 | 2.245 | 2 |
| 41.50 | 2.176 | 1 |
| 42.04 | 2.149 | 2 |
| 42.72 | 2.116 | 3 |
| 44.65 | 2.029 | 3 |
| 45.35 | 2.000 | 10 |
| 46.15 | 1.967 | 1 |
| 46.59 | 1.949 | 3 |
| 47.15 | 1.928 | 12 |
| 48.62 | 1.873 | 7 |
| 49.60 | 1.838 | 2 |
| 50.45 | 1.809 | 2 |
| 51.15 | 1.786 | 3 |
| 51.49 | 1.775 | 6 |
| 52.55 | 1.741 | 2 |
| 53.54 | 1.711 | 2 |
| 54.79 | 1.675 | 1 |
| 55.23 | 1.663 | 3 |
| 55.73 | 1.649 | 1 |
| 56.52 | 1.628 | 1 |
| 56.85 | 1.620 | 1 |
| 57.13 | 1.612 | 2 |
| 58.45 | 1.579 | 2 |
| 59.12 | 1.563 | 1 |
| 59.90 | 1.544 | 2 |

TABLE 3

X-Ray Diffraction Patterns of ZSM-35 Prepared in Example 8

| 2 Times Theta | d(A) | I/Io |
|---|---|---|
| 9.24 | 9.57 | 107 |
| 12.45 | 7.11 | 26 |
| 12.65 | 7.00 | 40 |
| 13.31 | 6.65 | 26 |
| 15.30 | 5.79 | 12 |
| 15.55 | 5.70 | 6 |
| 17.82 | 4.98 | 4 |
| 18.33 | 4.84 | 1 |
| 18.71 | 4.74 | 3 |
| 19.38 | 4.58 | 1 |
| 22.25 | 4.00 | 67 |
| 22.55 | 3.94 | 44 |

TABLE 3-continued

X-Ray Diffraction Patterns of ZSM-35 Prepared in Example 8

| 2 Times Theta | d(A) | I/Io |
|---|---|---|
| 23.09 | 3.85 | 28 |
| 23.50 | 3.79 | 52 |
| 23.79 | 3.74 | 9 |
| 24.31 | 3.66 | 30 |
| 25.10 | 3.55 | 100 |
| 25.60 | 3.48 | 83 |
| 26.35 | 3.38 | 15 |
| 26.89 | 3.32 | 17 |
| 28.42 | 3.14 | 27 |
| 29.28 | 3.05 | 15 |
| 30.25 | 2.954 | 8 |
| 30.86 | 2.897 | 7 |
| 31.40 | 2.849 | 3 |
| 33.02 | 2.713 | 5 |
| 33.82 | 2.650 | 8 |
| 34.20 | 2.622 | 2 |
| 34.75 | 2.582 | 3 |
| 35.28 | 2.544 | 2 |
| 36.25 | 2.478 | 6 |
| 36.58 | 2.456 | 1 |
| 37.30 | 2.411 | 4 |
| 37.56 | 2.395 | 2 |
| 38.33 | 2.348 | 3 |
| 39.00 | 2.309 | 3 |
| 39.41 | 2.286 | 2 |
| 39.92 | 2.258 | 2 |
| 40.25 | 2.240 | 3 |
| 41.52 | 2.175 | 1 |
| 42.13 | 2.145 | 3 |
| 42.82 | 2.112 | 3 |
| 44.72 | 2.026 | 5 |
| 45.45 | 1.996 | 11 |
| 46.19 | 1.965 | 1 |
| 46.56 | 1.950 | 4 |
| 47.21 | 1.925 | 11 |
| 48.75 | 1.868 | 8 |
| 49.75 | 1.833 | 3 |
| 50.55 | 1.806 | 3 |
| 51.28 | 1.782 | 3 |
| 51.55 | 1.773 | 7 |
| 52.62 | 1.739 | 2 |
| 53.70 | 1.707 | 2 |
| 54.90 | 1.672 | 2 |
| 55.32 | 1.661 | 3 |
| 55.75 | 1.649 | 1 |
| 56.57 | 1.627 | 1 |
| 56.90 | 1.618 | 2 |
| 57.31 | 1.608 | 3 |
| 58.55 | 1.576 | 2 |
| 59.10 | 1.563 | 1 |
| 59.80 | 1.546 | 2 |

Figure 2:
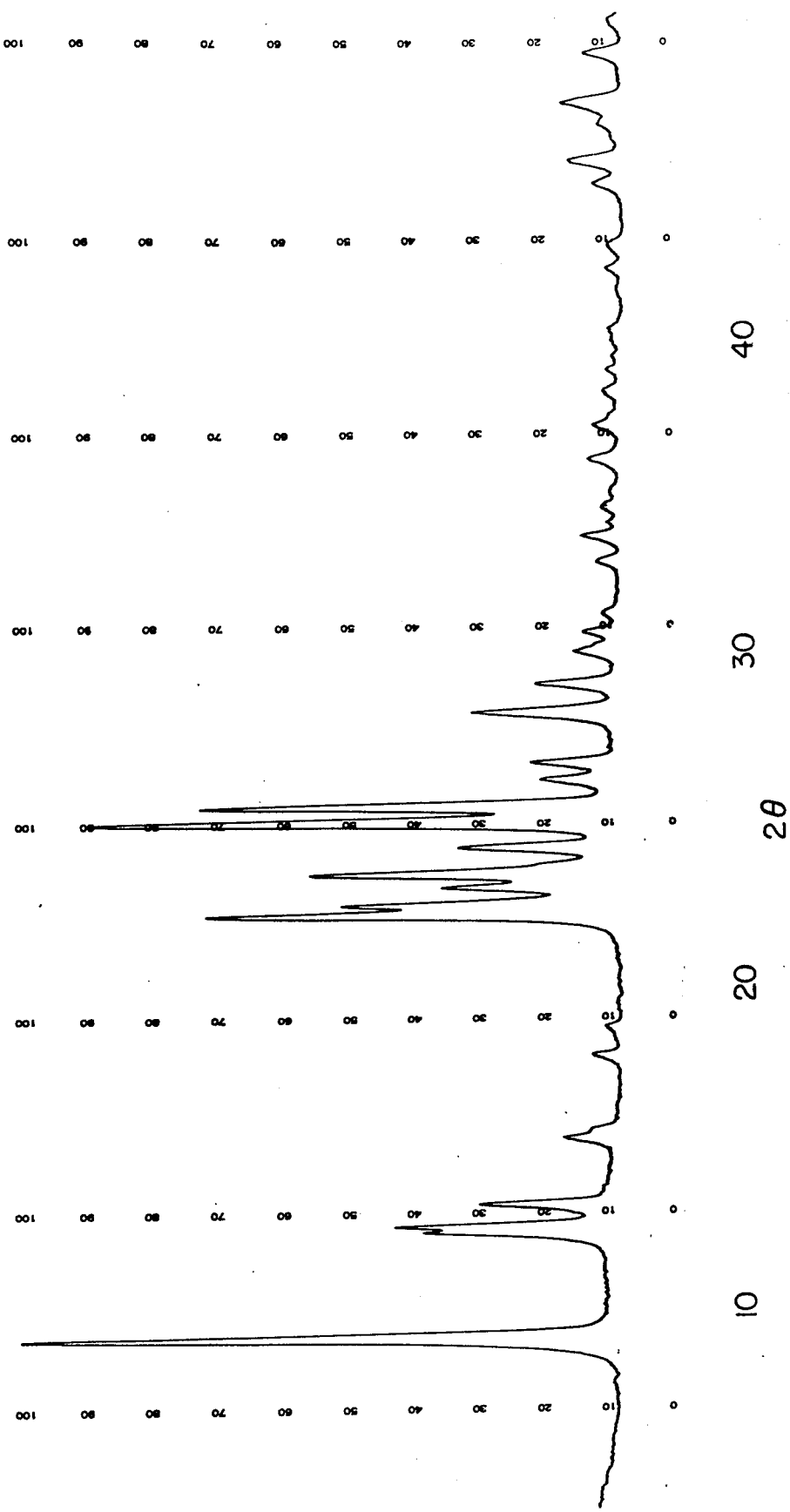
FIG. 2 is a photographically reduced copy of the X-ray powder diffraction pattern for the crystalline aluminosilicate zeolite ZSM-35 prepared in Example 6, hereinafter presented.
Figure 3:
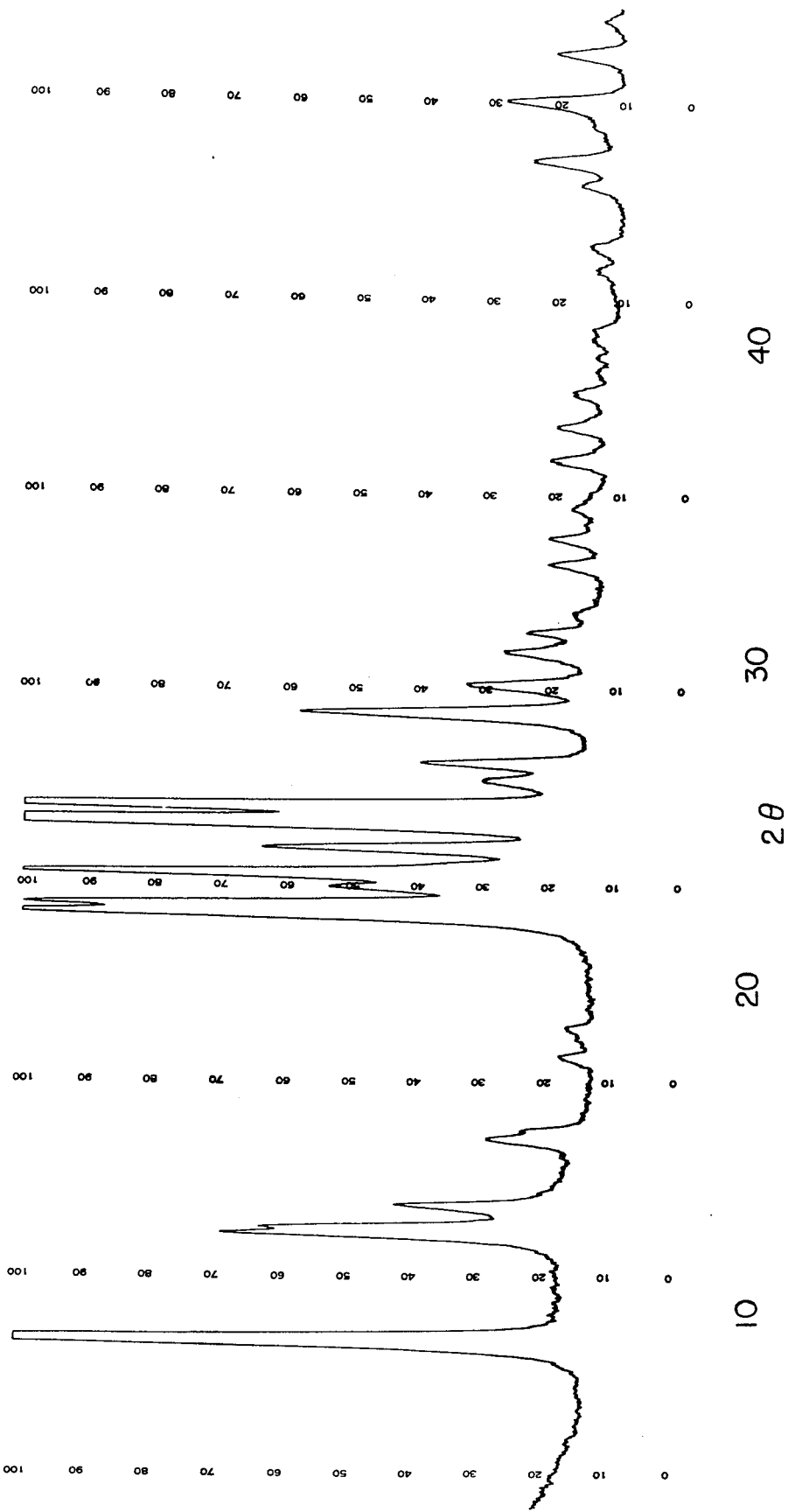
FIG. 3 is a photographically reduced copy of the X-ray powder diffraction pattern for the crystalline aluminosilicate zeolite ZSM-35 prepared in Example 7, hereinafter presented.
Figure 4:
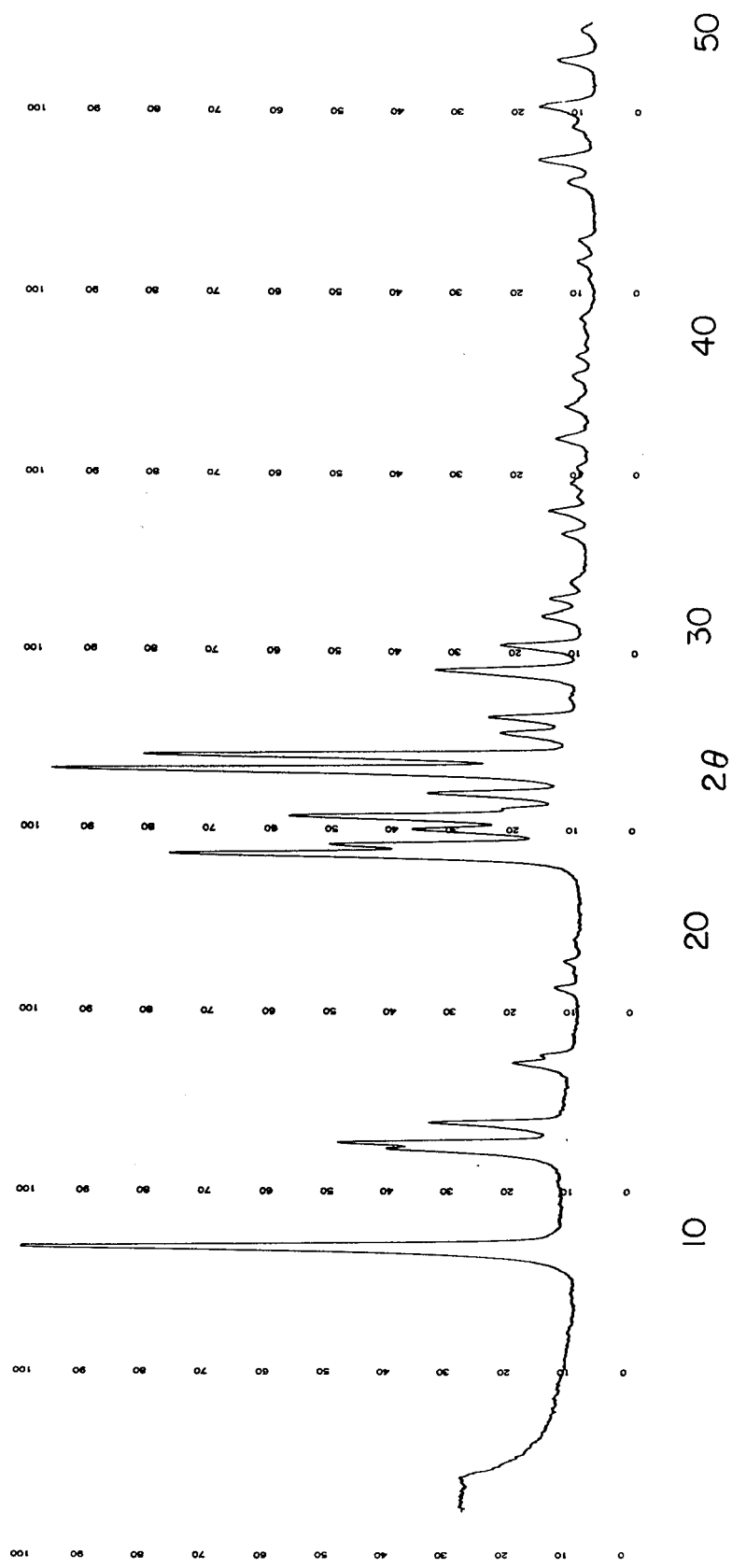
FIG. 4 is a photographically reduced copy of the X-ray powder diffraction pattern for the crystalline aluminosilicate zeolite ZSM-35 prepared in Example 8, hereinafter presented.

A photographically reduced exact copy of the X-ray diffraction pattern tracing for each zeolite ZSM-35 sample prepared in Examples 6, 7 and 8 is shown in FIGS. 2, 3 and 4, respectively, of the drawings.

Further examples are presented by way of tabular accumulation of data as follows in Tables 4, 4A, 5 and 5A. Tables 4 and 4A show examples of preparation of ZSM-35 while using ethylenediamine as the organic nitrogen-containing cation source, wherein R is $H_2N(C_2H_2)_2NH_2$ and M is sodium.

Tables 5 and 5A show examples of ZSM-35 preparation while using pyrrolidine as the source of organic nitrogen-containing cation. In each example of Tables 5 and 5A, $R^+$ is the pyrrolidine ion and M is sodium.

X-ray analysis of the products of each of the examples pesented in Tables 4, 4A, 5 and 5A proved them to have a diffraction pattern as shown in Table 1.

Figure 5:
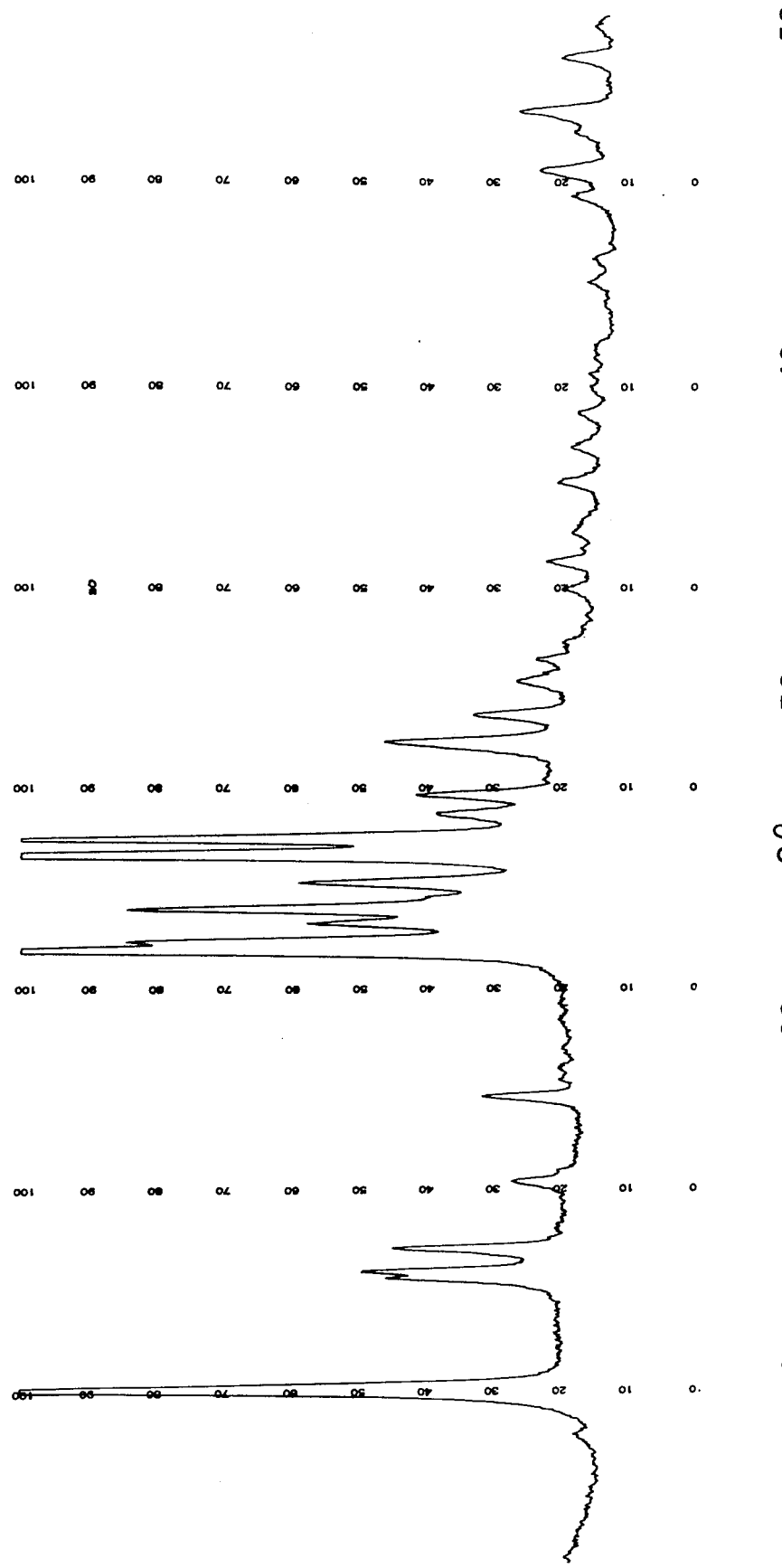
FIG. 5 is a photographically reduced copy of the X-ray powder diffraction pattern for the crystalline aluminosilicate zeolite ZSM-35 prepared in Example 18, hereinafter presented.
Figure 6:
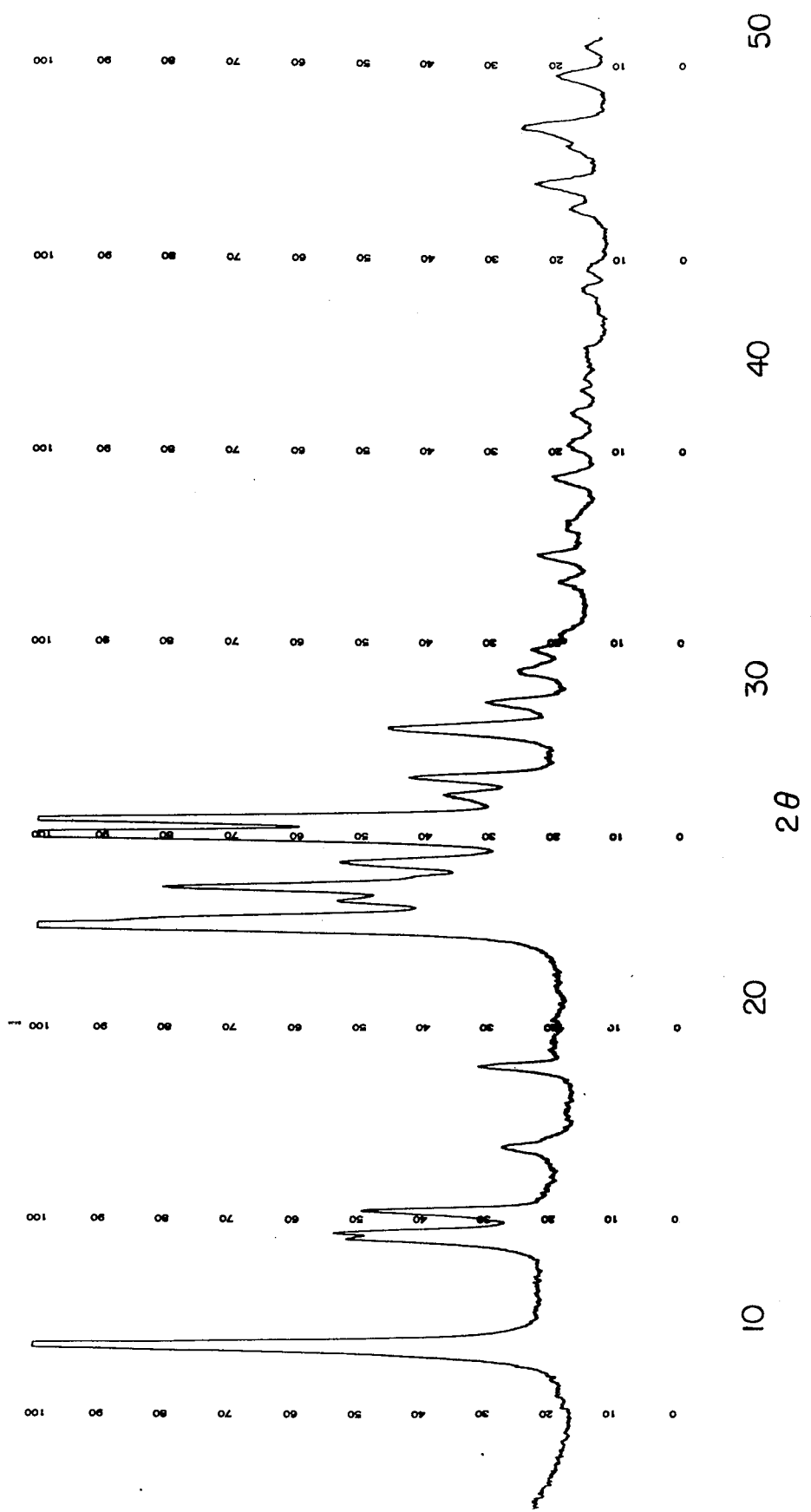
FIG. 6 is a photographically reduced copy of the X-ray powder diffraction pattern for the crystalline aluminosilicate zeolite ZSM-35 prepared in Example 19, hereinafter presented.

The full X-ray diffraction patterns for the zeolite ZSM-35 samples prepared in Examples 18 and 19 appear in Table 6 and a photographically reduced exact copy of the X-ray diffraction pattern tracings from the ZSM-35 samples of Examples 18 and 19 are shown in FIGS. 5 and 6, respectively, of the drawings.

TABLE 4

ZSM-35 SYNTHESIS FROM ETHYLENEDIAMINE

| Example | Preparation Notes | Starting Gel, Molar Ratio | | | | Crystallization | |
|---|---|---|---|---|---|---|---|
| | | $R^+/R^+ + M^+$ | $OH^-/SiO_2$ | $SiO_2/Al_2O_3$ | $H_2O/OH^-$ | Temp., °F | Time, Days |
| 9 | Components of Example 1(2) | 0.87 | 0.19 | 14.6 | 205 | 310 | 16 |
| 10 | Components of Example 1(2) | 0.89 | 0.15 | 16.2 | 244 | 210 | 150 |
| 11 | Components of Example 8 | 0.81 | 0.20 | 21.3 | 114 | 275 | 14 |
| 12 | Components of Example 8 | 0.81 | 0.20 | 21.3 | 114 | 350 | 5 |
| 13 | Components of Example 8 | 0.62 | 0.32 | 22.0 | 108 | 210 | 103 |
| 14 | Components of Example 8(1) | 0.88 | 0.87 | 32.4 | 224 | 310 | 11 |
| 15 | Components of Example 1(2) | 0.88 | 0.086 | 32.4 | 224 | 210 | 99 |
| 16 | Components of Example 8 | 0.62 | 0.30 | 33.4 | 109 | 210 | 41 |
| 17 | Components of Example 8 | 0.69 | 0.30 | 33.4 | 109 | 210 | 62 |

(1) Sodium aluminate and silica of formula: 87.5% $SiO_2$, 1.6% NaCl, 10.5% $H_2O$
(2) Components of zeolite preparation reaction mixture excluding the source of organic nitrogen-containing cation.

TABLE 4A

ZSM-35 SYNTHESIS FROM ETHYLENEDIAMINE

| | Final Product Analysis per mole $Al_2O_3$ | | | Final Product Sorption, wt. % | | | Surface Area |
|---|---|---|---|---|---|---|---|
| Example | $N_2O$ | $Na_2O$ | $SiO_2$ | $H_2O$ | $Cy-C_6$ | $n-C_6$ | $m^2/gm$ |
| 9 | 1.93 | 0.11 | 19.2 | 9.1 | 0.6 | 3.8 | 274 |
| 10 | 1.49 | 0.33 | 14.4 | 13.0 | 2.0 | 7.1 | 312 |
| 11 | | | | 11.4 | 0.8 | 5.7 | 312 |
| 12 | 1.6 | 0.05 | 14.8 | 10.6 | 0.9 | 6.4 | 293 |
| 13 | 1.51 | 0.05 | 17.1 | 12.7 | 2.6 | 7.3 | 352 |
| 14 | 1.45 | 0.07 | 16.7 | 9.8 | 0.5 | 4.5 | 260 |
| 15 | 2.0 | — | 25.9 | 8.5 | 3.8 | 9.0 | 343 |
| 16 | 1.84 | 0.11 | 20.0 | 8.4 | 1.8 | 6.2 | 323 |
| 17 | 1.95 | 0.24 | 20.9 | 10.3 | 0.4 | 5.8 | 295 |

TABLE 5

ZSM-35 SYNTHESIS FROM PYRROLIDINE

| Example | Preparation Notes | Starting Gel, Molar Ratio | | | | Crystallization | |
|---|---|---|---|---|---|---|---|
| | | $R^+/R^+ + M^+$ | $OH^-/SiO_2$ | $SiO_2/Al_2O_3$ | $H_2O/OH^-$ | Temp., °F | Time Days |
| 18 | Components of Example 1 | 0.88 | 0.28 | 8.82 | 195 | 350 | 10 |
| 19 | Components of Example 1 | 0.74 | 0.17 | 15.2 | 231 | 350 | 15 |
| 20 | Components of Example 1 | 0.74 | 0.17 | 15.2 | 231 | 275 | 11 |
| 21 | Components of Example 1 | 0.74 | 0.17 | 15.2 | 231 | 350 | 5 |
| 22 | Components of Example 1 | 0.87 | 0.097 | 29.0 | 202 | 270 | 17 |
| 23 | Components of Example 8 (1) | 0.50 | 0.49 | 33.3 | 70.5 | 210 | 36 |
| 24 | Components of Example 8 (1) | 0.68 | 0.32 | 33.6 | 108 | 210 | 27 |
| 25 | Components of Example 8 (1) | 0.62 | 0.13 | 48.0 | 333 | 304 | 7 |

(1) Components of zeolite preparation reaction mixture excluding the source of organic nitrogen-containing cation.

TABLE 5A

ZSM-35 SYNTHESIS FROM PYRROLIDINE

| | Final Product Analysis per mole $Al_2O_3$ | | | Final Product Sorption, wt. % | | | Surface Area |
|---|---|---|---|---|---|---|---|
| Example | $N_2O$ | $Na_2O$ | $SiO_2$ | $H_2O$ | $C_y-C_6$ | $nC_6$ | $m^2/gm$ |
| 18 | — | — | — | 10.5 | 2.1 | 7.6 | 370 |
| 19 | 0.89 | 0.28 | 18.6 | 10.0 | 0.8 | 4.6 | 235 |
| 20 | 0.77 | 0.28 | 14.0 | 11.5 | 2.3 | 7.0 | 306 |
| 21 | 0.74 | 0.25 | 14.1 | 10.0 | 1.1 | 6.3 | 246 |
| 22 | 1.40 | 0.07 | 29.1 | 11.0 | 2.1 | 8.2 | 349 |
| 23 | 0.68 | 0.28 | 14.3 | 8.3 | 3.9 | 4.3 | 346 |
| 25 | 0.81 | 0.58 | 37.1 | 6.9 | 1.1 | 2.5 | |

TABLE 6

X-Ray Diffraction Patterns of ZSM-35 Prepared in Example 18

| 2 Times Theta | d(A) | I/Io |
|---|---|---|
| 7.78 | 11.36 | 2 |
| 9.23 | 9.58 | 96 |
| 12.48 | 7.09 | 20 |
| 12.68 | 6.98 | 27 |
| 13.34 | 6.64 | 25 |
| 15.29 | 5.79 | 9 |
| 15.59 | 5.68 | 3 |
| 17.82 | 4.98 | 12 |
| 18.35 | 4.83 | 2 |
| 18.69 | 4.75 | 2 |
| 19.35 | 4.59 | 1 |
| 22.28 | 3.99 | 87 |
| 22.56 | 3.94 | 46 |
| 23.08 | 3.85 | 31 |
| 23.50 | 3.79 | 54 |
| 23.79 | 3.74 | 13 |
| 24.25 | 3.67 | 37 |
| 25.11 | 3.55 | 100 |
| 25.60 | 3.48 | 79 |
| 26.32 | 3.39 | 17 |
| 26.88 | 3.32 | 21 |
| 28.40 | 3.14 | 25 |
| 29.22 | 3.06 | 13 |
| 30.20 | 2.959 | 8 |
| 30.85 | 2.898 | 5 |
| 31.35 | 2.853 | 4 |
| 33.00 | 2.714 | 4 |
| 33.83 | 2.650 | 7 |
| 34.25 | 2.618 | 2 |
| 34.75 | 2.582 | 4 |
| 35.20 | 2.550 | 1 |
| 36.23 | 2.479 | 6 |
| 37.25 | 2.414 | 5 |
| 38.25 | 2.353 | 4 |
| 38.96 | 2.312 | 2 |
| 39.40 | 2.287 | 2 |
| 39.92 | 2.258 | 1 |

TABLE 6-continued
X-Ray Diffraction Patterns of ZSM-35 Prepared in Example 18

| 2 Times Theta | d(A) | I/Io |
|---|---|---|
| 40.23 | 2.242 | 3 |
| 41.52 | 2.175 | 1 |
| 42.15 | 2.144 | 3 |
| 42.80 | 2.113 | 3 |
| 44.69 | 2.028 | 5 |
| 45.42 | 1.997 | 9 |
| 46.09 | 1.969 | 2 |
| 46.60 | 1.949 | 5 |
| 47.17 | 1.927 | 12 |
| 48.75 | 1.868 | 7 |
| 49.71 | 1.834 | 3 |
| 50.52 | 1.807 | 3 |
| 51.25 | 1.782 | 3 |
| 51.51 | 1.774 | 6 |
| 52.59 | 1.740 | 2 |
| 53.63 | 1.709 | 2 |
| 54.90 | 1.672 | 1 |
| 55.24 | 1.663 | 2 |
| 55.60 | 1.653 | 2 |
| 56.60 | 1.626 | 2 |
| 56.94 | 1.617 | 2 |
| 57.34 | 1.607 | 2 |
| 58.38 | 1.581 | 1 |
| 58.70 | 1.573 | 1 |
| 59.07 | 1.564 | 1 |
| 59.83 | 1.546 | 2 |

TABLE 6
X-Ray Diffraction Patterns of ZSM-35 Prepared in Example 19

| 2 Times Theta | d(A) | I/Io |
|---|---|---|
| 9.25 | 9.56 | 88 |
| 12.49 | 7.09 | 17 |
| 12.69 | 6.98 | 22 |
| 13.35 | 6.63 | 26 |
| 15.30 | 5.79 | 8 |
| 15.60 | 5.68 | 3 |
| 17.85 | 4.97 | 10 |
| 18.41 | 4.82 | 2 |
| 18.78 | 4.72 | 2 |
| 19.37 | 4.58 | 2 |
| 22.26 | 3.99 | 78 |
| 22.55 | 3.94 | 31 |
| 23.09 | 3.85 | 21 |
| 23.49 | 3.79 | 41 |
| 23.75 | 3.75 | 10 |
| 24.25 | 3.67 | 31 |
| 25.10 | 3.55 | 100 |
| 25.55 | 3.49 | 74 |
| 26.30 | 3.39 | 16 |
| 26.85 | 3.32 | 19 |
| 28.40 | 3.14 | 22 |
| 29.22 | 3.06 | 9 |
| 30.21 | 2.958 | 7 |
| 30.84 | 2.899 | 6 |
| 31.36 | 2.852 | 3 |
| 33.00 | 2.714 | 4 |
| 33.84 | 2.649 | 7 |
| 34.25 | 2.618 | 2 |
| 34.73 | 2.583 | 3 |
| 35.00 | 2.564 | 1 |
| 35.26 | 2.545 | 2 |
| 36.24 | 2.479 | 6 |
| 36.77 | 2.444 | 2 |
| 37.25 | 2.414 | 4 |
| 37.60 | 2.392 | 1 |
| 38.22 | 2.355 | 4 |
| 38.97 | 2.311 | 3 |
| 39.35 | 2.290 | 2 |
| 39.82 | 2.264 | 1 |
| 40.23 | 2.242 | 3 |
| 41.52 | 2.175 | 1 |
| 42.15 | 2.144 | 3 |
| 42.80 | 2.113 | 3 |
| 44.69 | 2.028 | 5 |
| 45.42 | 1.997 | 9 |
| 46.09 | 1.969 | 2 |
| 46.60 | 1.949 | 5 |
| 47.17 | 1.927 | 12 |

TABLE 6-continued
X-Ray Diffraction Patterns of ZSM-35 Prepared in Example 19

| 2 Times Theta | d(A) | I/Io |
|---|---|---|
| 48.75 | 1.868 | 7 |
| 49.71 | 1.834 | 3 |
| 50.52 | 1.807 | 3 |
| 51.25 | 1.782 | 3 |
| 51.51 | 1.774 | 6 |
| 52.59 | 1.740 | 2 |
| 53.63 | 1.709 | 2 |
| 54.90 | 1.672 | 1 |
| 55.24 | 1.663 | 2 |
| 55.60 | 1.653 | 2 |
| 56.60 | 1.626 | 2 |
| 56.94 | 1.617 | 2 |
| 57.34 | 1.607 | 2 |
| 58.38 | 1.581 | 1 |
| 58.70 | 1.573 | 1 |
| 59.07 | 1.564 | 1 |
| 59.83 | 1.546 | 2 |

What is claimed is:

1. A synthetic crystalline aluminosilicate zeolite having a composition in the anhydrous state, expressed in terms of mole ratios of oxids as follows:

$$(0.3-2.5)R_2O:(0-0.8)M_2O : Al_2O_3 : >8\ SiO_2$$

wherein R is an organic nitrogen-containing cation derived from ethylenediamine or pyrrolidine and M is an alkali metal cation and having an X-ray powder diffraction pattern as that shown in Table 1 of the specification, the sorption capacity of said zeolite after calcination at 600° C being characterized by the ratio of normal hexane sorption to 2-methylpentane sorption at 90° C of less than 10.

2. A synthetic crystalline aluminosilicate zeolite according to claim 1 having a composition in the anhydrous state, expressed in terms of mole ratios of oxides as follows:

$$(0.4-2.5)R_2O:(0-0.6)M_2O : Al_2O_3 : x\ SiO_2$$

wherein x is from greater than 8 to about 50.

3. A synthetic crystalline aluminosilicate zeolite according to claim 1 wherein R is the organic cation derived from ethylenediamine.

4. A synthetic crystalline aluminosilicate zeolite according to claim 1 wherein R is the organic cation derived from pyrrolidine.

5. A synthetic crystalline aluminosilicate zeolite according to claim 1 wherein M is sodium.

6. A synthetic crystalline aluminosilicate zeolite according to claim 3 wherein M is sodium.

7. A synthetic aluminosilicate zeolite according to claim 4 wherein M is sodium.

8. A method for preparing the crystalline aluminosilicate zeolite defined in claim 1 which comprises preparing a mixture containing sources of an alkali metal oxide, an organic nitrogen-containing oxide, an oxide of aluminum, an oxide of silicon and water and having a composition, in terms of mole ratios of oxides, falling within the following ranges:

| | |
|---|---|
| $\dfrac{R^+}{R^+ + M^+}$ | 0.2–1.0 |
| $OH^-/SiO_2$ | 0.05–0.5 |
| $H_2O/OH^-$ | 41–500 |

| $R^+$ | |
|---|---|
| $SiO_2/Al_2O_3$ | 8.8–200 | wherein R is an organic nitrogen-containing cation derived from ethylenediamine or pyrrolidine and M is an alkali metal ion, maintaining the mixture at a temperature of at least 90° F until the crystals of said aluminosilicate are formed.

9. The method of claim 8 wherein the mixture has a composition, in terms of mole ratios of oxides, falling within the following ranges:

| $\dfrac{R^+}{R^+ + M^+}$ | 0.3–0.9 |
|---|---|
| $OH^-/SiO_2$ | 0.07–0.49 |
| $H_2O/OH^-$ | 100–250 |

| $R^+$ | |
|---|---|
| $SiO_2/Al_2O_3$ | 12–60 |

10. The method according to claim 8 wherein the temperature is maintained between about 90° and about 400° F.

11. The method according to claim 9 wherein the temperature is maintained between about 150° and about 400° F.

12. A synthetic crystalline aluminosilicate zeolite comprising the zeolite of claim 1 having its original cations replaced, at least in part, by ion exchange with a cation or a mixture of cations selected from the group consisting of hydrogen and hydrogen precursors, rare earth metals, aluminum, and metals from Groups IIA, IIIA, IVA, IB, IIB, IIIB, IVB, VIB, and VIII of the Periodic Table of the Elements.

13. The synthetic crystalline aluminosilicate zeolite of claim 12 wherein said replacing cation is hydrogen of a hydrogen precursor.

* * * * *

UNITED STATES PATENT AND TRADEMARK OFFICE
CERTIFICATE OF CORRECTION

PATENT NO. : 4,016,245
DATED : April 5, 1977
INVENTOR(S) : CHARLES J. PLANK, EDWARD J. ROSINSKI and MAE K. RUBIN It is certified that error appears in the above-identified patent and that said Letters Patent are hereby corrected as shown below:

| | |
|---|---|
| Column 3, line 39 | "ration" should read --ratio--. |
| Column 4, Table | The first ratio listed in the table should be -- $\frac{R^+}{R^+ + M^+}$ --. |
| Column 6, line 3 | "exchanger" should read --exchange--. |
| Column 6, line 20 | After the word "synthesized" insert the word --form--. |
| Column 6, line 66 | "McNanee" should read --McNamee--. |
| Column 10, line 20 | "exchange" should read --exchanged--. |

Signed and Sealed this

Sixth Day of September 1977

[SEAL]

Attest:

RUTH C. MASON
Attesting Officer

LUTRELLE F. PARKER
Acting Commissioner of Patents and Trademarks